United States Patent [19]

Hope et al.

[11] Patent Number: 5,252,263
[45] Date of Patent: Oct. 12, 1993

[54] INDUCTION OF ASYMMETRY IN VESICLES

[75] Inventors: Michael J. Hope; Pieter R. Cullis, both of Vancouver, Canada

[73] Assignee: The Liposome Company, Inc., Princeton, N.J.

[21] Appl. No.: 854,107

[22] Filed: Mar. 17, 1992

Related U.S. Application Data

[60] Division of Ser. No. 61,837, Jun. 12, 1987, Pat. No. 5,204,112, which is a continuation-in-part of Ser. No. 874,575, Jun. 16, 1986, abandoned.

[51] Int. Cl.$^5$ .................... B01J 13/00; A61K 9/127
[52] U.S. Cl. ........................... 264/4.3; 424/450; 264/4.1
[58] Field of Search ............... 264/4.1, 4.3; 424/450

[56] References Cited

U.S. PATENT DOCUMENTS

| Re. 31,609 | 6/1984 | Sears | 424/450 |
|---|---|---|---|
| 3,962,429 | 6/1976 | Furuno et al. | 514/14 |
| 3,993,754 | 11/1976 | Rahman et al. | 424/450 X |
| 4,145,410 | 3/1979 | Sears | 264/4.1 X |
| 4,193,983 | 3/1980 | Ullman et al. | 424/450 X |
| 4,217,344 | 8/1980 | Van der Berghe et al. | 264/4.1 X |
| 4,224,179 | 9/1980 | Schneider et al. | 264/4.6 |
| 4,235,871 | 11/1980 | Papahadjopoulos et al. | 424/450 |
| 4,241,046 | 12/1980 | Papahadjopoulos et al. | 424/450 X |
| 4,389,330 | 6/1983 | Tice et al. | 264/4.1 X |
| 4,411,894 | 10/1983 | Schrank et al. | 514/221 |
| 4,438,052 | 3/1984 | Weder et al. | 264/4.6 |
| 4,485,045 | 11/1984 | Regan | 264/4.3 X |
| 4,515,736 | 5/1985 | Deamer | 264/4.3 |
| 4,522,803 | 6/1985 | Lenk et al. | 424/1.1 |
| 4,588,578 | 5/1986 | Fountain et al. | 424/1.1 |
| 4,619,794 | 10/1986 | Hauser | 264/4.3 X |
| 4,663,161 | 5/1987 | Mannino et al. | 424/450 X |
| 4,721,612 | 1/1988 | Janoff et al. | 264/4.1 X |
| 4,762,720 | 8/1988 | Jizomoto | 424/450 |
| 4,975,282 | 12/1990 | Bally et al. | 264/4.1 X |
| 5,008,050 | 4/1991 | Cullis et al. | 264/4.3 |
| 5,077,056 | 12/1991 | Bally et al. | 424/450 |
| 5,192,549 | 3/1993 | Barenolz et al. | 424/450 |

FOREIGN PATENT DOCUMENTS

| 0088046 | 7/1983 | European Pat. Off. |
| 85/00968 | 3/1985 | World Int. Prop. O. |
| 86/00238 | 1/1986 | World Int. Prop. O. |
| 86/01102 | 2/1986 | World Int. Prop. O. |
| 86/01103 | 2/1986 | World Int. Prop. O. |
| 87/00043 | 1/1987 | World Int. Prop. O. |
| 87/02219 | 4/1987 | World Int. Prop. O. |

OTHER PUBLICATIONS

Bally, et al., 1985, Biochim. Biophys. Acta., 812:66, "Uptake of safranine and other lipophilic cations into model membrane systems in response to membrane potential".

(List continued on next page.)

Primary Examiner—Robert L. Stoll
Assistant Examiner—John M. Covert
Attorney, Agent, or Firm—Allen Bloom; Kenneth B. Rubin

[57] ABSTRACT

Methods are described for controlling the transbilayer distribution of ionizable lipids and proteins in vesicles. Control of the ion gradient of the exterior bathing medium in relation to that of the interior entrapped aqueous compartment of the vesicles induces migration of ionizable lipids or proteins to one or the other of the monolayers comprising the bilayer. This can result in an asymmetric distribution of the ionizable lipid or ionizable protein. The basic ionizable lipids, such as stearylamine and sphingosine, are sequestered into the inner monolayer when the liposome interior is acidic relative to the liposome exterior. Conversely, acidic ionizable lipids such as oleic acid and stearic acid are sequestered into the inner monolayer when the liposome interior is basic relative to the liposome exterior bathing solution. Likewise, phospholipids such as phosphatidylglycerol, phosphatidylinositol, and cardiolipin may also be sequestered into the inner monolayer in response to a relatively acidic exterior medium. Such vesicles may contain bioactive agents and may be administered to mammals including humans.

42 Claims, 4 Drawing Sheets

OTHER PUBLICATIONS

Bangham, et al., "Diffusion of Univalent Iona Across the Lamellae of Swolle Phospholipids", 1965; J. Mol. Biol., 13:238-252.

Brecher, et al., 1984, J. Biol. Chem. 21:133955, "Fatty Acid Transfer between Multilamellar Liposomes and Fatty Acid-binding Proteins".

Ganong, et al., 1984, Biochem., 23:4977, "Transmembrane Movement of Phosphatidylglycerol and Diacylglycerol".

Hamilton, et al., 1986, Proc. Natl. Acad. Sci, USA: 83:82, "Transfer of olec acid between albumin and phospholipid vesicles".

Homan, Reynold, Membrane Asymmetry in Phospholipid Vesicles, (Dissertation, State Univ. of NY at Stony Brook), 1985.

Hope, et al., J. Biochim. Biophys. Acta., 812:55-65, "Production of large unilamellate vesciles by a rapid extrusion procedure. Characterization of size distribution, trapped volume and ability to maintain a membrane potential".

Hope, et al., "Chem. Abst 106(21):171514g (1987)".

Houslay, et al., 1982, John Wiley and Sons, Toronto, pp. 178-205, "Dynamics of Biological Membranes".

Kates, M., 1972: Techniques in Lipidology: Isolation, Analysis, and Identification of Lipids, Elsevier, N.Y., 1972.

Lentz, et al., "Transbilayer Redistribution of Phosphatidylglycerol in Small, Unilamellar Vesicles Induced by Specific Divalent Cations", Biochemistry 18, 1982.

Litman, Chem. Abst. 81(25): 165154p (1974).

Mayer, et al., "Uptake of antineoplastic agents into large unilamellar vesicles in response to a membrane potential", 1985; Biochem. Biophys. Acta., 816:294-302.

Mayer, et al., 1985, J. Biol. Chem., 260:802, "Uptake of Dibucaine into Large Unilamellar Vesicles in Response to a Membrane Potential".

Nicholls, et al., Academic Press, Inc., N.Y. 1982, Bioenergetics: "An Introduction to the Chemiosmotic Theory".

Op den Kemp, 1979, Ann. Rev. Biochem., 48:47, "Lipid Asymmetry in Membranes".

Pagano, et al., Chem. Abst. 92(23):193118a (1979).

Pagano, et al., Chem. Abst. 95(11):92686r (1981).

Papahadjopoulos, et al., "Phospholipid Model Membranes, Structural Characteristics of Hydrated Liquid Crystals", 1967; Biochim. Biophys. Acta., 135:624-638.

Rothman, et al., 1977, Science, 195:743-753, "Membrane Asymmetry".

Tyurin, et al., Chem. Abst. 109(17):144930r (1988).

Crommelin, et al., "Preparation and characterization of doxorubicin-containing liposome: I. Influence of liposome charge and pH of hydration medium on loading capacity and particle size", Int. J. Pharms. 16, (1983), 79-92.

Crommelin, et al., "Preparation and characterization of doxorubicin-containing liposomes, II. Loading capacity, long-term stability and doxorubicin-bilayer interaction mechanism", Chemical Abstracts, vol. 100, 1984, Abs. 109032w.

Garcia, et al.; "Mechanism of lactose translocation in proteoliposomes reconstituted with lac carrier protein purified from *Escherishia coli*", Biol. Abs. vol. 77(7), 1984.

Groom, et al., "Liposomes", Chem. Abs., vol. 102, 1985, Abs #67398d.

Kirby, et al., "Dehydration-rehydration vesicles: a simple method of high yield drug entrapment in liposomes", Chem. Abs. vol. 102, 1985, Abs #84326w.

Moro, et al., "Purification of Liposome Suspensions", Chem. Abs. vol. 94, 1981 p. 372, Abs. 52931g.

Shakhov, et al., "Reconstitution of highly purified proton-translocating pyrophosphate from Rhocuspirillium rubrum", Biological Abstracts 77(12), 1984.

Van Hoesel, et al., "Reduced cardiotoxicity and nephrotoxicity with preservation of antitumor activity of doxorubicin entrapped in stable liposomes in the LOU/M", Chem. Abs. vol. 101, 1984 163307y.

U.S. Ser. No. 4,762 filed on Jan. 1987 to Cullis et al., abandoned.

U.S. Ser. No. 360,964 filed on Jun. 1989 to Janoff et al., pending.

INDUCTION OF ASYMMETRY IN VESICLES

The present application is a divisional application of copending application Ser. No. 07/061,837 filed Jun. 12, 1987, now U.S. Pat. No. 5,204,112 which is a continuation-in-part application of Ser. No. 874,575, filed Jun. 16, 1986, now abandoned.

BACKGROUND OF THE INVENTION

The present invention is directed to a method for controlling the transbilayer distributions of ionizable lipids or ionizable proteins in a vesicle bilayer. More particularly, the invention describes methods for localizing ionizable lipids or ionizable proteins to either the inner or outer monolayer of unilamellar vesicles or to that of the outermost bilayer of multilamellar vesicles (MLV) in response to transmembrane ion gradients.

Liposomes are completely closed lipid bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (non-polar) "tails" of the lipid monolayers orient toward the center of the bilayer while the hydrophilic (polar) "heads" orient towards the aqueous phase.

The original liposome preparation of Bangham et al. (J. Mol. Biol., 13, 238-252 1965) involves suspending phospholipids in an organic solvent which is then evaporated to dryness leaving a phospholipid film on the reaction vessel. Then an appropriate amount of aqueous phase is added, the mixture is allowed to "swell", and the resulting liposomes which consist of multilamellar vesicles (MLVs) are dispersed by mechanical means. This technique provides the basis for the development of the small sonicated unilamellar vesicles described by Papahadjopoulos et al. (*Biochim. Biophys. Acta.* 135, 624-638 1967), and large unilamellar vesicles.

Large unilamellar vesicles may be produced using an extrusion apparatus by a method described in Cullis et al., PCT 87/00238, Jan. 16, 1986, entitled "Extrusion Technique for Producing Unilamellar Vesicles," relevant portions of which are incorporated herein by reference. Vesicles made by this technique, LUVETS, are extruded under pressures of up to about 700 psi through a polycarbonate membrane filter. These vesicles may be exposed to at least one freeze and thaw cycle prior to the extrusion technique; this procedure is described in Bally et al., PCT 87/00043, Jan. 15, 1987, entitled "Multilamellar Liposomes Having Improved Trapping Efficiencies", relevant portions of which are incorporated herein by reference.

Another class of liposomes that may be used are those characterized as having substantially equal lamellar solute distribution. This class of liposomes is denominated as stable plurilamellar vesicles (SPLV) as defined in U.S. Pat. No. 4,522,803 to Lenk, et al., monophasic vesicles as described in U.S. Pat. No. 4,558,579 to Fountain, et al., and frozen and thawed multilamellar vesicles (FATMLV) wherein the vesicles are exposed to at least one freeze and thaw cycle; this procedure is described in Bally et al., PCT Publication No. 87/00043, Jan. 15, 1987, entitled "Multilamellar Liposomes Having Improved Trapping Efficiencies" and incorporated herein by reference.

A variety of sterols and their water soluble derivatives have been used to form liposomes; see specifically Janoff et al., PCT 85/04578, Oct. 24, 1985, entitled "Steroidal Liposomes". Mayhew et al., WO 85/00968, published Mar. 14, 1985, described a method for reducing the toxicity of drugs by encapsulating them in liposomes comprising alpha-tocopherols and certain derivates thereof. Also, a variety of tocopherols and their water soluble derivatives have been used to form liposomes, see Janoff et al., PCT 87/02219, Apr. 23, 1987, entitled "Alpha-Tocopherol-Based Vesicles" and incorporated herein by reference.

The method for preparing the sterol vesicles involving adding to an aqueous buffer a salt form of an organic acid derivative of a sterol capable of forming closed bilayers in an amount sufficient to form completely closed bilayers which entrap an aqueous compartment. A suspension of multilamellar vesicles is formed by shaking the mixture. The formation of vesicles is faciliated if the aqueous buffer also contains the counterion of the salt in solution.

The application of energy to the suspension, e.g., sonication, or extrusion of the vesicles through a French pressure cell (French Press) or through a filter of the appropriate pore size, will convert the multilamellar sterol vesicles to unilamellar vesicles.

The present invention provides a method for producing vesicles, preferably unilamellar vesicles, that exhibit transbilayer asymmetry of lipid in response to a transmembrane pH gradient. Alternatively, MLVs may also be made to exhibit this asymmetry in their outermost bilayer.

There is an ongoing need for liposomes having enhanced pharmacokinetics, sustained released characteristics, stability and targeting ability.

SUMMARY OF THE INVENTION

The present invention describes methods for making liposomes in which the distribution of an ionizable lipid or protein component can be controlled between the monolayers of the outer bilayer of the liposomes. Such distribution may be made to be asymmetric. The liposomes of the invention have an outer bilayer which contains an ionizable lipid or an ionizable protein in an asymmetrical distribution between the monolayers of the outer bilayer. The ionizable lipid may be basic, as an amine such as sphingosine or stearylamine, or acidic, as in the phospholipids phosphatidyglycerol, phosphatidylinositol, or cardiolipin, a prostaglandin, or the fatty acids such as oleic acid or stearic acid. The ionizable protein may be basic. Several types of liposomes may be used in the practice of the invention, such as FATMLVs, MPVs, or SPLVs. The liposomes of the invention may also be exposed to an extrusion technique. Alternatively, the liposomes may be unilamellar.

The liposomes may also contain a bioactive agent, and the bioactive agent itself may be ionizable. The liposomes may be administered to mammals such as humans.

The liposomes of the invention are multilamellar or unilamellar. Multilamellar liposomes may be made by any method known in the art and include SPLVs, freeze and thaw MLVs, REVs, and MPVs. Unilamellar liposomes may be formed by a freeze and thaw technique followed by an extrusion through polycarbonate filters.

The liposomes may contain bioactive agents, such as ionizable drugs. Such ionizable drugs may themselves be loaded into the liposomes according to an ion concentration gradient across the bilayer. Alternatively, drugs may simply be loaded during the aqueous entrapment step of the liposome-forming procedure. Liposomes of the invention may also be dehydrated for long term storage in stable form until rehydration and use. The liposomes may be administered to mammals such as humans.

DETAILED DESCRIPTION OF THE INVENTION

The following abbreviations will be employed:
DOPE—dioleoyl phosphatidylethanolamine
DOPC—dioleoyl phosphatidylcholine
PE—phosphatidylethanolamine
PS—phosphatidylserine
PC—phosphatidylcholine
SM—sphingomyelin
BSA—bovine serum albumin
PI—phosphatidylinositol
PG—phosphatidylglycerol
CL—cardiolipin
REV—reverse phase evaporation vesicle
MPV—monophasic vesicle
MLV—multilamellar vesicle
SUV—small unilamellar vesicle
LUV—large unilamellar vesicle
LUVET—large unilamellar vesicles made by extrusion technique
HEPES—N-2-hydroxyethyl piperazine-N'-2-ethane sulfonic acid
TNBS—trinitrobenzene sulphonic acid
MTPP$^+$—methyltriphenylphosphonium cation
TNP-PE—trinitrophenylated phosphatidylethanolamine The liposomes of the present invention are unilamellar vesicles, preferably large unilamellar vesicles. However, small unilamellar vesicles and multilamellar vesicles may also be used.

The lipids that may be used in the present invention are ionizable lipids. Ionizable lipids include those which are acidic and basic and may be deprotonated or protonated, at a pH of between about 2.0 and about 14.0 in an aqueous environment. Upon protonation or deprotonation, lipids become charged lipids. Such ionizable lipids include, but are not limited to phosphatidylglycerol, phosphatidic acid, and their derivatives, the amine-containing lipids phosphatidylserine, phosphatidylethanolamine and phosphatidylinositol; stearylamine, sphingosine, cardiolipin, and the fatty acids. Fatty acids of all chain lengths and degrees of unsaturation may be used; for example those fatty acids having about 6 to about 22 carbon atoms, most preferably about 12 to about 18 carbon atoms and having about 0 to about 4 double bonds, most preferably having about 0 to about 1 double bond such as stearic acid and oleic acid. Other ionizable lipids (bilayer components) that may be used are the bile acids and prostaglandins. The prostaglandins include their precursor substances arachidonic acid and its metabolites as well as their structural analogs, and synthetic enzyme inhibitors. The term prostaglandin also includes synthetic compounds structurally related to the naturally occurring prostaglandins, as well as the prostacyclines and leukotrienes.

Still other ionizable bilayer components that may be used are the salt forms of organic acid derivatives of sterols or tocopherols, preferably cholesterol or tocopherol hemisuccinates respectively. Neutral lipids, being those that possess no net charge or are not ionizable at the pH employed, that may be used in the invention include, but are not limited to phospholipids such as phosphatidylcholine, dioleoylphosphatidylcholine, sphingomyelin, cholesterol, and their derivatives. Non-lipid materials, such as ionizable proteins (the term "protein" includes peptides or polypeptides) may also be used. Such proteins (which include peptides and polypeptides) also include those with substituted amino acids, compared to the naturally occurring material, in their chains, as well as derivatives, analogs, and fragments of the proteins. Such proteins include those that are acidic or basic, and can be protonated or deprotonated. Such proteins include, but are not limited to, alpha, beta, and gamma interferons, interleukin 2, interleukin 1, colony-stimulating factors, tumor necrosis factor, the histone proteins, and the growth hormones such as bovine growth hormone, human growth hormone and porcine growth hormone. These proteins all have ionizable groups and are therefore useful for the practice of the present invention. Most preferably used in the present invention are the proteins oxytocin, vasopressin, arginine vasopressin, calcitonin, and alpha-atrial natriuritic factor.

During preparation of the liposomes, organic solvents may be used to suspend the lipids. Suitable organic solvents are those with a variety of polarities and dielectric properties, which solubilize the lipids, and include but are not limited to chloroform, methanol, ethanol, dimethylsulfoxide (DMSO), methylene chloride, and solvent mixtures such as benzene:methanol (70:30). As a result, solutions (mixtures in which the lipids and other components are uniformly distributed throughout) containing the lipids are formed. Solvents are chosen on the basis of their biocompatibility, low toxicity, and solubilization abilities.

Liposomes entrap an aqueous medium which is enclosed by the lipid bilayers. The aqueous medium can be for example, water or water containing a dissolved salt or buffer. Examples of such salts or buffers can be sodium chloride and phosphate buffered saline (PBS). Other buffers include but are not limited to borate, citrate, Tris-HCl tris-(hydroxymethyl)- aminomethane hydrocholoride), and HEPES (N-2-hydroxyethyl piperazine-N'-2-ethane sulfonic acid). Buffers may be in the pH range of between about 2.0 and about 14.0. In the preferred embodiment, the preparations are hydrated with HEPES buffer (150 mM NaCl, 20 mM HEPES), pH 7.0, borate buffer (100 mM $Na_2HCO_3$, 50 mM $H_3BO_3$, pH 8.5, or citrate buffer (150 mM Na-citrate), pH 8.5.

In a liposome-drug delivery system, the medicament is entrapped in the liposome and then administered to the patient to be treated. For example, see Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179, Lenk, et al., U.S. Pat. No. 4,522,803, and Fountain et al., U.S. Pat. No. 4,588,578.

Virtually any bioactive agent can be entrapped within the liposomes for use according to the present invention. Such agents include but are not limited to antibacterial compounds such as gentamycin, antiviral compounds such as rifampacin, antifungal compounds such as amphotericin B, anti-parasitic compounds such as antimony derivatives, antineoplastic compounds such as vinblastine, vincristine, mitomycin C, doxorubicin, daunomycin, methotrexate, and cisplatinum, among others, proteins such as albumin, toxins such as diptheria toxin, enzymes such as catalase, hormones such as estrogens, neurotransmitters such as acetylcholine, lipoproteins such as alpha-lipoprotein, glycoproteins such as hyaluronic acid, immunoglobulins such as IgG, immunomodulators such as the interferons or the interleukens, dyes such as Arsenazo III, radiolabels such as $^{14}C$, radio-opaque compounds such as $^{99}Te$, fluorescent compounds such as carboxy fluoroscein, polysaccharides such as glycogen, cell receptor binding molecules such as estrogen receptor protein, non-steroidal anti-inflammatories such as indomethacin, salicylic acid acetate, ibuprofen, sulindac, piroxicam, and naproxen; anti-inflammatories such as dexamethasone, antiglaucomic agents such as timolol or pilocarpine, anesthetics such as dibucaine, nucleic acids such as thymine, polynucleotides such as RNA polymers.

The liposomes of the present invention may be dehydrated, thereby enabling storage for extended periods of time until use. Standard freeze-drying equipment or equivalent apparatus may be used to dehydrate the liposomes. Liposomes may also be dehydrated simply by placing them under reduced pressure. Alternatively, the liposomes and their surrounding medium can be frozen in liquid nitrogen prior to dehydration. Dehydration with prior freezing may be performed in the presence of one or more protective sugars in the preparation, according to the procedures of Janoff et al., PCT 86/01103, Feb. 27, 1986, entitled "Dehydrated Liposomes", relevant portions of which are incorporated herein by reference. Examples of protective sugars that may be used include but are not limited to trehalose, maltose, sucrose, glucose, lactose and dextran. Alternatively, multilamellar vesicles may be dehydrated with prior freezing with or without protective sugars. When the dehydrated liposomes are to be used, rehydration is accomplished by simply adding an aqueous solution, e.g., distilled water, to the liposomes and allowing them to rehydrate.

According to the present invention, vesicles containing ionizable lipids or ionizable proteins (weak acids or weak bases) are made in an aqueous environment of controlled pH, then exposed to a bathing medium of a relatively more acidic or relatively more basic pH. Thus, a concentration gradient is formed across the membrane with the internal aqueous (entrapped) medium being of a different pH than that of the external aqueous (bathing) medium.

The phenomenon of transfer of weak acids or weak bases across an essentially impermeable lipid membrane across which exists a pH gradient proceeds as described by the Henderson Hasselbach equation. As a result, in a unilamellar vesicle, the charged lipids will migrate to one monolayer preferentially over the other to achieve this Henderson-Hasselbach equilibrium constant (Nicholls, In:Bioenergetics: An Introduction to the Chemiosmotic Theory, Academic Press, N.Y. 1982) resulting in liposomes having asymmetric bilayers. For example, when the interior aqueous medium of the vesicles is acidic with respect to the external aqueous medium, lipids that can be protonated, such as stearylamine and sphingosine are immediately sequestered into the inner monolayer. Alternatively, results consistent with a localization of acidic lipids such as phosphatidylglycerol (PG), phosphatidylinositol (PI), cardiolipin, the bile acids, prostaglandins, and the fatty acids oleic acid and stearic acid, to the inner monolayer are observed for vesicles whose internal aqueous media are basic with respect to the external aqueous medium. In multilamellar vesicles, the outermost bilayer will reflect this asymmetry.

More specifically, as applied to liposomes, the distribution of weak acids and weak bases, including lipids and bioactive agents across the bilayer membrane is based on their abilities to permeate the membranes when in the neutral form, achieving transmembrane concentrations obeying the Henderson-Hasselbach equilibrium equation:

$$\frac{[AH^+]_i}{[AH^+]_o} = \frac{[H^+]_i}{[H^+]_o}$$

where $AH^+$ refers to a protonated lipid or bioactive agent such as one containing a protonated amine; the subscripts i and o refer to the interior and exterior of the vesicle respectively. In the case of amine-containing lipids such as stearylamine and sphingosine, or basic bioactive agents, their localization to the membrane results in similar redistributions where the transbilayer location of the protonated amine reflects the interior and exterior proton concentration at the membrane interfaces.

The ability of pH gradients to markedly influence the transmembrane distributions of these amine-containing lipids demonstrate that the transmembrane distributions of lipids which are weak acids, such as some phospholipids and fatty acids, are also strongly dependent on transmembrane pH gradients. Since the neutral (protonated) form can permeate the membrane, this will result in transmembrane gradients according to:

$$\frac{[RCOO^-]_i}{[RCOO^-]_o} = \frac{[H^+]_o}{[H^+]_i}$$

where $RCOO^-$ refers to the unprotonated fatty acid. In vesicles exhibiting pH gradients where the interior is basic, fatty acids therefore move to the interior monolayer.

Ionizable lipids or proteins are also translocated and ionizable agents loaded into liposomes according to a $Na^+/K^+$ concentration gradient. In such cases, $Na^+/K^+$ diffusion potentials existing across the membrane allow an ionized species to go into the membrane in place of a $K^+$ ion that diffuses out.

The method of the invention requires the formation of liposomes at a controlled pH, including an ionizable lipid or ionizable protein. For example, such charged lipids may be stearylamine or sphingosine, or phospholipids or fatty acids such as oleic or stearic acid. The ionizable lipids may be in a proportion of from about 1 mol % to about 50 mol % of the total lipid used to form the liposomes, preferably 5-10 mol %. The ionizable lipids may be in a proportion of up to about a 1:1 mol ratio.

The labeling agent TNBS may be used to trace the transbilayer migration of the ionizable lipids. To the hydrated lipids of choice, following formation of liposomes, was added an aliquot of the labelling agent TNBS, whose reactivity with amino groups of either peptides or phospholipids may be quantitated chromatographically or spectrophotometrically. TNBS-labelled liposomes containing charged lipid were exposed to bathing media of differing pH than that of the formation buffer (relatively more acidic or basic). Where the ionizable lipid or bioactive agent to be translocated is negatively charged, the formation buffer will be basic, at pH from about 8.0 to about pH 14.0 preferably about pH 8.0 to about pH 11.0, most preferably about pH 10.0. After formation, the liposomes are exposed to buffer or more acidic pH, at pH about 2.0 to about pH 7.5 preferably about pH 2.0 to about pH 6.0, most preferably about pH 5.0.

Alternatively, when the lipid to be translocated was positively charged, the formation buffer used was acidic, at pH about 2.0 to about pH 7.5, most preferably pH 5.0. After formation, the liposomes were exposed to buffer of more basic pH, about pH 7.5 to about pH 14.0, most preferably about pH 8.0. Such exposure of the liposomes to the alternate pH buffer may take place either on a gel filtration column, or directly, by immersion of vesicles directly in the buffer.

When the lipid to be translocated across the bilayer is a phospholipid, such as phosphatidylclycerol, phosphatidylinositol, or cardiolipin, the following procedure is followed. The liposomes are formed, containing the ionizable phospholipids, by any of the above-mentioned methods in the art for forming liposomes, preferably unilamellar liposomes, and containing buffer at pH 8.0, for example, 300 mM phosphate buffer. The thus-labeled liposomes containing the charged (ionizable) lipid were then exposed to bathing media of differing pH than that of the formation medium. Since the phospholipids to be translocated are negatively charged, the formation buffer is basic, at a pH of about 6.0 to about 10.0, preferably about pH 8.0. After liposome formation, the liposomes are exposed to buffer of more acidic pH, i.e., about pH 3.0 to about 6.0, preferably about pH 4.0. Simultaneous to the acidification of the medium, the liposome suspension is heated to about 30° C. to about 60° C., for about 10 minutes. When the suspension is heated to about 37° C., the suspension is held at that temperature for about 12 hours. The suspension is then cooled to about 25° C.

The same procedures used for translocating ionizable lipids can be employed for ionizable proteins. Preferantial translocation of the charged lipid to one or the other monolayers was spectrophotometrically detected by labelling of the amino-containing lipid by TNBS. Alternatively, the asymmetry may be demonstrated by ion exchange using DEAE sephacel ion exchange (see Example 8).

The liposomes of the present invention may also be remote loaded with ionizable agents according to the disclosure of Bally et al., PCT 86/01102, Feb. 26, 1986, entitled "Encapsulation of Antineoplastic Agents in Liposomes", relevant portions of which are incorporated herein by reference. In this procedure, a transmembrane potential is created across the bilayers of the liposomes during formation, and the ionizable agent is loaded into the liposomes by means of the transmembrane potential. This potential is generated by creating a concentration gradient for one or more charged species (e.g., $Na^+$, $K^+$ and/or $H^+$) across the liposome membranes. Alternatively in the present invention, the inner monolayer of the liposome may already be charged due to transmembrane migration of a ionizable lipid or ionizable protein to the inner monolayer. Ionizable bioactive agents may be loaded in response to this charge, while the membrane asymmetry of the liposomes entrapping these agents changes in response to this charge imposed by the gradient. Thus, it is possible to effect both processes simultaneously i.e.: loading of the liposomes with ionizable agent and inducing asymmetry in the liposome membrane. Both processes may be controlled by the pH gradient applied to the liposomes. For each pH unit of difference applied between the internal and the external aqueous solutions, there is a ten-fold difference in the encapsulation of the ionizable agent (lipid, protein, and drug) (10:1, inside:outside). As the pH difference increases to two units difference, the inside: outside concentration of the ionizable agent increases to 100:1, and so on for three and more units of pH difference. Ionizable lipids or proteins or entrapped ionizable agents are translocated to the inner monolayer of the bilayer in question (i.e.: the single bilayer of a unilamellar liposomes, or the outermost bilayer of a multilamellar liposome) in response to this gradient.

The medicaments are administered within liposomes, in admixture with a pharmaceutically-acceptable carrier selected with regard to the intended route of administration and standard pharmaceutical practice. Dosages for these medicaments when entrapped in liposomes will be about that of the drugs alone; dosages will be set by the prescribing physician with regard to the age, weight, and condition of the patient. The proportional ratio of active ingredient to carrier will naturally depend on the chemical nature, solubility, and stability of the active ingredient, as well as the dosage contemplated. For the oral mode of administration, a liposome composition of this invention can be used in the form of tablets, capsules, lozenges, troches, powders, syrups, elixirs, aqueous solutions and suspensions, and the like.

In the case of tablets, carriers which can be used include lactose, sodium citrate, and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, certain sweetening and/or flavoring agents can be added. For parenteral administration or injection via intravenous, intraperitoneal, intramuscular, subcutaneous, or intra-mammary route sterile solutions of the liposome composition are prepared. For intravenous use, the total concentration of solutes should be controlled to render the preparation isotonic.

In another example of their use, vesicle-entrapped compounds may be incorporated into a broad range of topical dosage forms including but not limited to gels, oils, emulsions and the like. For instance, the suspension containing the entrapped compound may be added to the aqueous phase as an ingredient in the liposome preparation. Such preparations may be administered as topical creams, pastes, ointments, gels, lotions and the like for direct application.

Alternatively, the liposomes of the present invention may be used as in vitro diagnostic agents.

The following examples are given for purposes of illustration only and not by way of limitation on the scope of the invention.

MATERIALS AND METHODS

Lipids

Phosphatidylglycerol, dioleoylphosphatidylcholine (DOPC) and dioleoylphosphatidyl- ethanolamine (DOPE) were purchased from Avanti Polar Lipids (Birmingham, Ala.). [$^{14}$C]-labelled DOPE was prepared from DOPC and [$^{14}$C]- ethanolamine (both obtained from New England Nuclear (NEN), Boston, Mass.) using phospholipase D to exchange the choline head group for ethanolamine. The resulting [$^{14}$C]-labelled DOPE was purified on CM cellulose. Cholesterol, stearylamine, sphingosine, stearic acid and oleic acid were obtained from Sigma (St. Louis) and used without further purification. [$^{3}$H]-dipalmitoyl phosphatidylcholine ([$^{3}$H]-DPPC), [$^{14}$C]-oleic acid and [$^{14}$C]-stearic acid were also purchased from NEN.

EXAMPLE 1

Preparation of Vesicles

Large unilamellar vesicles were prepared by extrusion techniques as in Hope et al., *Biochim. Biophys. Acta*, 812, p. 55-65 (1985). The extrusion device was obtained from Lipex Biomembranes Inc., Vancouver, Canada. For chromatographic analysis following chemical labelling studies, DOPC and 10 mol % [$^{14}$C]-DOPE were mixed in chloroform and dried to a film under vacuum. Buffer (150 mM NaCl, 20 mM HEPES, pH 7.0) was added to the dried film to give a liposomal suspension of 10 umoles phospholipid/ml. The liposomes were then freeze-thawed five times employing alternate liquid nitrogen and warm water cycles as described in Bally et al., U.S. patent application, Ser. No. 800,545, filed Nov. 21, 1985, entitled "Multilamellar Liposomes Having Improved Trapping Efficiencies", relevant portions of which are incorporated herein by reference. The vesicles were subsequently extruded ten times through two stacked 0.1 um pore size polycarbonate filters (Nuclepore) as described by Cullis et al., U.S. application Ser. No. 788,017, filed Oct. 16, 1985, entitled "Extrusion Technique for Producing Unilamellar Vesicles", relevant portions of which are incorporated herein by reference. The resulting LUVs exhibited an average diameter of 100 nm (as determined by light scattering techniques) and a trapped volume of approximately 1.5 ul/umol phospholipid.

TEST PROCEDURE

Chromatographic Assay for TNBS Labelling of PE

Figure 1:
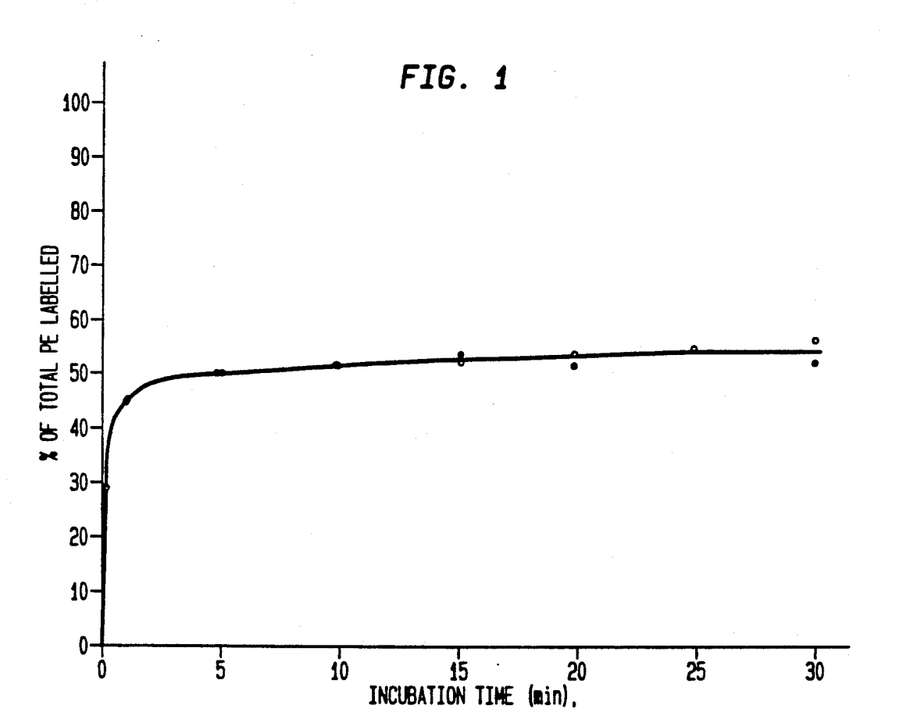
FIG. 1 is a graph showing the time course for the reaction of TNBS with vesicles of DOPC containing 10 mol % DOPE. Labelling was determined by either chromatographic (closed circles) or spectrophotometric (open circles) methods.

DOPC and DOPE (1:9 mol ratio containing trace amounts of [$^{14}$C]-DOPE) were mixed in chloroform and LUVs prepared as described in Example 1. Two umoles of the vesicle suspension (200 ul) were added to 800 ul of 0.5 mM Trinitrobenzene sulphonic acid (TNBS) (Sigma) in 100 mM sodium bicarbonate (NaHCO$_3$), 50 mM hydrogen borate (H$_2$BO$_3$), pH 8.5. The mixture was incubated at room temperature for 30 minutes and 20 ul of 20 mM ethanolamine were added (to quench the TNBS reaction) with mixing. After 1 minute, 200 ul of 1M HCl were added, the mixture was vortexed and left to stand for approximately 2 minutes. Lipid was extracted from the aqueous mixture employing the Bligh and Dyer extraction procedure (Kates, M., In: *Techniques in Lipidology: Isolation, Analysis and Identification of LIpids*, Elsevier, N.Y. 1972). The resulting chloroform extract was dried under nitrogen and resuspended in 50 ul of chloroform. The total extract was applid to pre-coated silica gel 60 thin layer chromatography plates (20 cm×20 cm) and subsequently developed in a running solvent consisting of chloroform/methanol/27% ammonia solution/water (900:300:57:53, v/v). When the chromatogram was complete, the plates were dried and sprayed with a solution of 0.2% Ninhydrin in saturated butanol. The glass plates were developed by heating until the distinct pink spots of amino containing lipid could be seen. The trintrophenylated phosphatidylethanolamine (TNP-PE) was visible as a yellow spot near the solvent front. PE and TNP-PE were well separated and the silica gel containing the two lipids was aspirated directly into 4 ml of chloroform/methanol/water (60:40:10, v/v). After vortexing, the silica was pelleted by centrifugation at 500 g for 2 minutes, and the solvent decanted into 20 ml scintillation vials. The silica pellet was extracted once more and the combined solvent dried under nitrogen at 50° C. The acitvity of each sample was determined employing a Packard 2000CA scintillation analyzer (United Technologies, California). This procedure established the validity of the TNBS labelling procedures for assaying transmembrane distributions of lipids containing primary amino groups in large unilamellar vesicle systems. Fifty percent of the PE in DOPE:-DOPC (1:9 mol ratio) LUVs in the absence of pH gradients were labelled employing this chromatographic assay procedure. As shown in FIG. 1, the TNBS-PE reaction was essentially complete within 10 minutes and proceeds to an equilibrium value of 52+/−4%, consistent with an equilibrium transmembrane distribution of PE.

EXAMPLE 2

Spectrophotometric Assay for TNBS Labelling

DOPC was mixed in chloroform with 10 mol % DOPE, and dried under vacuum. The lipids were resuspended in buffer to a concentration of 20 umoles/ml at pH 8.5 (100 mM NaHCO$_3$, 50 mM H$_2$BO$_3$). The vesicles were produced as in Example 1 and were passed down gel filtration columns (15×1.5 cm) containing Sephadex G50 (Pharmacia or Sigma) equilibrated with 100 mM NaHCO$_3$, 50 mM H$_2$BO$_3$ at pH 8.5. A double beam spectrophotometer (Pye Unicam SP8-500, Philips) was employed to follow the TNBS labelling of available primary amine groups on the vesicles. A reference cuvette containing 2.5 ml of buffer (pH 8.5) was placed in the reference beam. The sample cuvette contained 2.5 ml of buffer (pH 8.5) containing 0.5 mM TNBS. Absorbance at 420 nm was followed to establish a base line and subsequently 0.1 to 0.5 ml aliquots of vesicles were added to each cuvette. The increase in absorbance at 420 nm was recorded until the reaction was complete. Two hundred ul of Triton X-100 detergent (0.5%) was added to both cuvettes to solubilize the vesicles and thus expose all amino groups present to TNBS. The absorbance in the presence of detergent was taken as 100% labelling.

The above procedure was repeated for lipids resuspended in buffer of pH 5.0 (150 mM sodium-citrate).

FIG. 1 shows the time course for the vesicle-TNBS reaction where the DOPC vesicles contain 10 mol % DOPE, as determined spectrophotometrically.

EXAMPLE 3

The materials and procedures of Example 1 were employed using DOPC-stearylamine (5 mol %) vesicles.

Figure 2A:
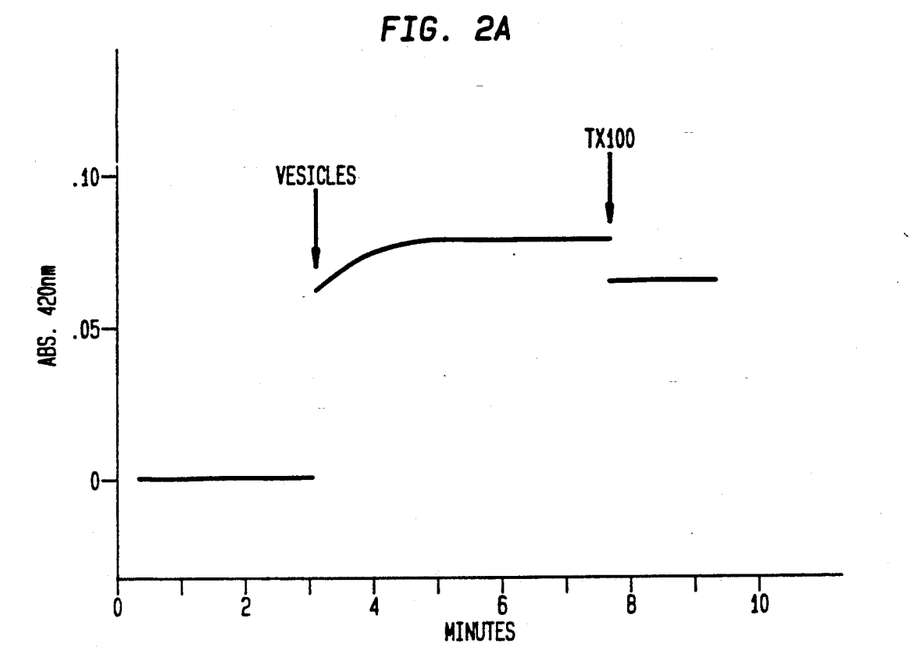
FIG. 2A is a graph showing the labelling of stearylamine by TNBS in DOPC vesicles where both the interior entrapped aqueous medium and exterior bathing medium is pH 8.5

FIG. 2A shows the TNBS labelling of stearylamine proceeding to completion as assayed spectrophotometrically (see Exampe 1), when the pH of the entrapped aqueous solution and the bathing medium were both pH 8.5. This demonstrates the rapid redistribution of inner monolayer stearylamine to the outer monolayer as the outer monolayer stearylamine is depleted on reaction with TNBS.

Figure 2B:
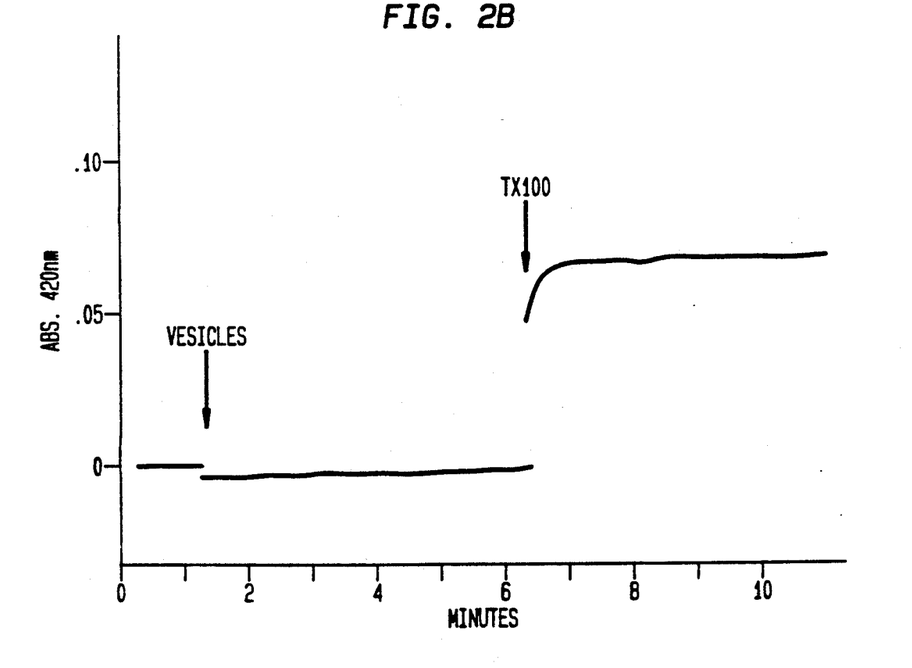
FIG. 2B is a graph showing the influence of a proton gradient across the vesicle bilayer (interior entrapped aqueous medium pH 5.0, exterior bathing medium pH 8.5) on the labelling of stearylamine to TNBS in DOPC vesicles.

FIG. 2B shows labelling in the presence of a pH gradient, (entrapped aqueous solution pH 5.0, bathing medium pH 8.5). No labelling of stearylamine could be detected within 10 minutes. Subsequent addition of 200 ul of Triton X-100 detergent (TX-100) to solubilize the vesicles resulted in complete labelling within 20 seconds. These results are consistent with a localization of stearylamine to the inner monolayer in response to the pH gradient.

EXAMPLE 4

The materials and procedures of Example 3 were employed using DOPC-sphingosine (5 mol %) vesicles.

Figure 3A:
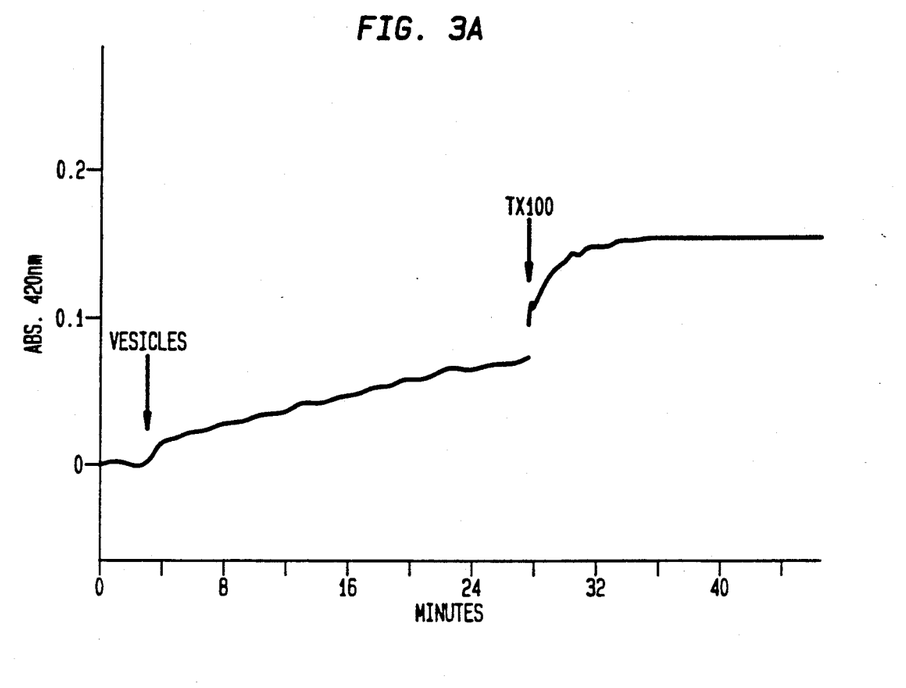
FIG. 3A is a graph showing labelling of sphingosine to TNBS in DOPC vesicles where both the interior entrapped aqueous medium and exterior bathing medium is pH 8.5.

FIG. 3A shows the result of LUVs that do not exhibit a proton gradient (pH 8.5: both internal and external buffer). This demonstrates the rapid redistribution of inner monolayer sphingosine to the outer monolayer as the outer monolayer sphingosine is depleted on reaction with TNBS.

Figure 3B:
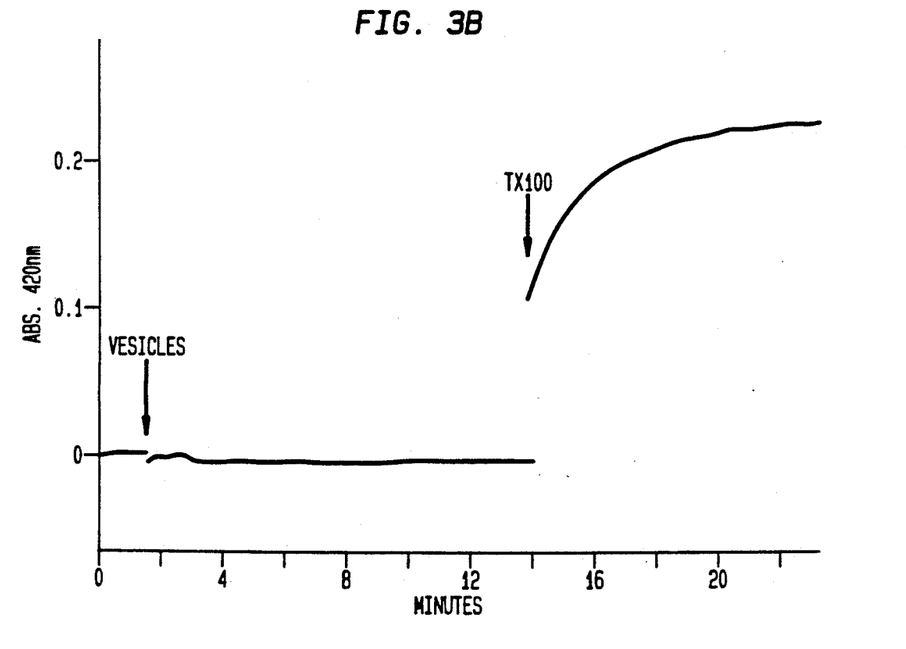
FIG. 3B is a graph showing the influence of a proton gradient across the vesicle bilayer (interior entrapped aqueous medium pH 5.0, exterior bathing medium pH 8.5) on the labelling of sphingosine to TNBS in DOPC vesicles.

FIG. 3B shows the result of LUVs that exhibit a proton gradient, pH 5.0 inside and pH 8.5 outside. These results are consistent with a localization of sphingosine to the inner monolayer in response to the pH gradient.

EXAMPLE 5

Analysis of Fatty Acid Distributions

DOPC was mixed with 10 mol % [$^{14}$C]-oleic acid and trace amounts of [$^3$H]-DPPC, in chloroform. The mixture was dried under vacuum and the lipid resuspended in 150 mM NaCl, 20 mM HEPES at pH 7.0. The liposomes were freeze-thawed and vesicles produced as in Example 1. The vesicles were passed down Sephadex G50 columns pre-equilibrated with 150 mM NaCl, 20 mM HEPES at pH 7.0. Two hundred ul of a solution of fat-free bovine serum albumin (BSA), (sigma) was added to 1 ml of the resulting vesicle preparation to give a final protein concentration of 5 mg/ml. The vesicle-albumin mixture was applied to a 15×1.5 cm column containing Sepharose 4B gel (Pharmacia) pre-equilibrated in buffer at pH 7.0. Fractions (0.5 ml) were collected, transferred to scintillation vials and activities determined using a [$^3$H]/[$^{14}$C] dual label program employing the Packard 2000CA scintillation analyzer.

The above procedures were repeated, resuspending the dried lipid in 150 mM H$_2$BO$_3$ at pH 10.

Figure 4A:
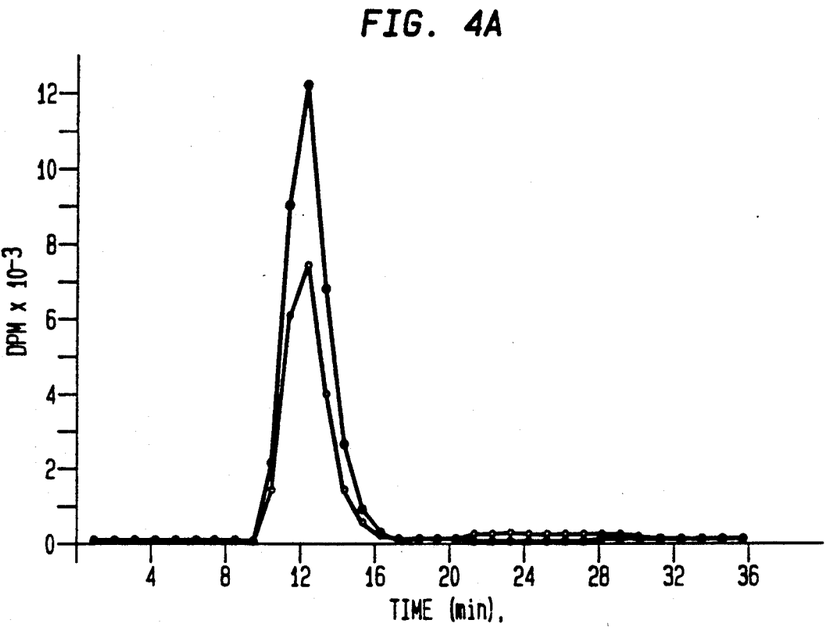
FIG. 4A is a graph showing ability of BSA to extract [$^{14}$C] oleic acid from LUVs when the interior entrapped aqueous medium is pH 10.0, and the external bathing medium is pH 7.0. The peak represents vesicles (closed circles) and oleic acid (open circles).

FIG. 4A shows removal of only a small amount of oleic acid by BSA when a transmembrane pH gradient (entrapped aqueous medium pH 10.0, exterior bathing medium pH 7.0) is present.

Figure 4B:
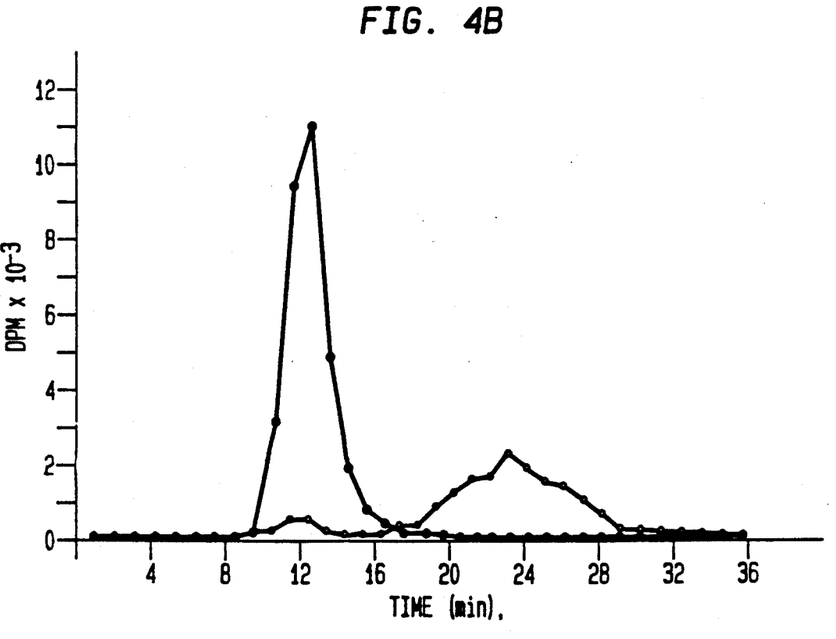
FIG. 4B is a graph showing ability of BSA to remove [$^{14}$C] oleic acid from LUVs when both the interior entrapped aqueous medium and the exterior bathing medium are both at pH 7.0. The peaks represent vesicles (closed circles) and oleic acid (open circles).

FIG. 4B shows almost complete removal of oleic acid by BSA when both the interior entrapped medium and the exterior bathing medium are the same (pH 7.0). This is consistent with a localization of the oleic acid to the inner monolayer in the presence of a proton gradient (interior basic).

EXAMPLE 6

The procedures of Example 5 were employed using DOPC mixed with 10 mol % of [$^{14}$C]-stearic acid and trace amounts of [$^3$H]-DPPC, in chloroform. Results similar to those of Example 4 employing oleic acid, were observed.

EXAMPLE 7

Liposomes containing 20 mg/ml EPC and 5 mol % PG (approx. 1.0 mg/ml) were formed according to the procedures of Example 1. The lipid film was hydrated in 2.0 ml of 300 mM phosphate buffer at pH 8.0. The external buffer was then changed to pH 4.0 by titration with 6M sulphuric acid or by gel filtration to exchange the external buffer for 150 mM citrate pH 4.0. The liposome suspension was heated at 60° C. for 30 minutes and the first external medium was simultaneously replaced by the more acidic external medium. Following the 30 minute heating step, the liposome suspension was cooled to 25° C. Results similar to those obtained in Example 4 employing oleic acid, were observed.

Movement of PG to the inner monolayer was demonstrated by ion exchange chromatography. The ionic strength of the external medium was reduced to approximately 10 mM by gel filtration prior to passing the liposomes through a column of DEAE sephacel. Liposomes with PG located at the inner monolayer exhibit less negative surface charge than liposomes with a random distribution of PG. Consequently liposomes with an asymmetric distribution of PG passed through the DEAE sephacel column with the void volume. Liposomes that do not exhibit PG asymmetry bind to the DEAE and are not eluted until the column is washed with high ionic strength buffer (see Example 8).

EXAMPLE 8

The liposomes of Example 7 (0.5 ml, having 50 umol/ml phospholipid) were passed down a gel filtration column (15×1.5 cm.) containing Sephadex G-50 equilibrated with 10 mM HEPES (pH 7.0). The liposomes were added to DEAE-Sephacel (Pharmacia), the flow rate adjusted to 1-2 ml/min., and 1.0 ml fractions collected. Liposomes bound to the column material were eluted employing 0.5M NaCl, 10 mM HEPES ao pH 7.0. Fractions were counted in a Packard 2000CA scintillation analyzer.

Liposome pH gradients were dissipated employing nigericin and valinomycin each at a concentration of 1 ug/umol lipid followed by the addition of 100 mM KCl to a final concentration of 1 mM.

EXAMPLE 9

The procedures and materials of Example 3 were employed, and ion exchange chromatography was used to determine the migration of the lipid to the inner monolayer, as in Example 8.

The liposomes of Example 3 (0.5 ml, having 50 umol/ml phospholipid) were passed down a gel filtration column (10×1.5 cm.) containing Sephadex G-50 equilibrated with 10 mM HEPES (pH 7.0). The liposomes were added to CM-Sepharose, CL-6B (Pharmacia), the flow rate adjusted to 1-2 ml/min., and 1.0 ml fractions collected. Liposomes bound to the column material were eluted employing 0.5 M NaCl, 10 mM HEPES at pH 8.5. Fractions were counted in a Packard 2000CA scintillation analyzer.

Liposome pH gradients were dissipated by subjecting the vesicles to to five cycles of freezing and thawing followed by resizing using the LUVET process.

What is claimed is:

1. A method for obtaining asymmetric liposomes having an outer bilayer which comprises an ionizable lipid or an ionizable protein wherein the outer bilayer has an asymmetric distribution of the ionizable lipid or ionizable protein within the two monolayers which comprise the outer bilayer, wherein the method comprises the steps of:
   (a) preparing liposomes with an internal aqueous buffer of between about pH 2.0 and about pH 7.5; and
   (b) exposing the liposomes of step (a) to an external aqueous buffer of between about pH 8.0 and about pH 14.0 to obtain the asymmetric liposomes.

2. The method of claim 1 wherein the ionizable lipid is basic.

3. The method of claim 1 wherein the ionizable lipid is an amine.

4. The method of claim 3 wherein the amine is sphingosine or stearylamine.

5. The method of claim 1 wherein the ionizable lipid is acidic.

6. The method of claim 5 wherein the ionizable lipid is a fatty acid.

7. The method of claim 6 wherein the fatty acid is oleic acid or stearic acid.

8. The method of claim 1 wherein the ionizable protein is basic.

9. The method of claim 8 wherein the ionizable protein is oxytocin, vasopressin, arginine vasopressin, calcitonin or alpha-atrial natriuritic factor.

10. The method of claim 1 wherein the liposomes are multilamellar liposomes.

11. The method of claim 10 wherein the liposomes are FATMLVs, MPVs, or SPLVs.

12. The method of claim 11 wherein the liposomes are FATMLVs.

13. The method of claim 11 wherein the liposome's aqueous layers have equal solute distribution.

14. The method of claim 2 comprising the additional step of extruding the liposomes of step (a).

15. The method of claim 2 wherein the liposomes are unilamellar vesicles.

16. The method of claim 2 wherein the liposomes additionally comprise a bioactive agent.

17. The method of claim 16 wherein the bioactive agent is ionizable.

18. A method for obtaining asymmetric liposomes having an outer bilayer which comprises an ionizable lipid or an ionizable protein wherein the outer bilayer has an asymmetric distribution of the ionizable lipid or ionizable protein within the two monolayers which comprise the outer bilayer, wherein the method comprises the steps of:
   (a) preparing liposomes with an internal aqueous buffer of between about pH 8.0 and about pH 11.0; and
   (b) exposing the liposomes of step (a) to an external aqueous buffer of between about pH 5.0 and about pH 7.5 to obtain the asymmetric liposomes.

19. The method of claim 18 wherein the ionizable lipid is acidic.

20. The method of claim 18 wherein the ionizable lipid is a fatty acid.

21. The method of claim 20 wherein the fatty acid is oleic acid or stearic acid.

22. The method of claim 18 wherein the ionizable lipid is basic.

23. The method of claim 18 wherein the ionizable lipid is an amine.

24. The method of claim 23 wherein the amine is sphingosine or stearylamine.

25. The method of claim 18 wherein the ionizable protein is basic.

26. The method of claim 18 wherein the ionizable protein is oxytocin, vasopressin, arginine vasopressin, calcitonin or alpha-atrial natriuritic factor.

27. The method of claim 18 wherein the liposomes are multilamellar liposomes.

28. The method of claim 27 wherein the liposomes are FATMLVs, MPVs, or SPLVs.

29. The method of claim 28 wherein the liposomes are FATMLVs.

30. The method of claim 27 wherein the liposome's aqueous layers have equal solute distribution.

31. The method of claim 18 comprising the additional step of extruding the liposomes of step (a).

32. The method of claim 31 wherein the liposomes are unilamellar vesicles.

33. The method of claim 32 wherein the liposomes additionally comprise a bioactive agent.

34. A method for obtaining asymmetric liposomes having an outer bilayer which comprises an ionizable phospholipid wherein the outer bilayer has an asymmetric distribution of the ionizable phospholipid between the two monolayers which comprise the outer bilayer, wherein the method comprises the steps of:
   (a) preparing liposomes with an internal aqueous buffer having a pH of between about 6.0 and about 10.0,
   (b) exposing the liposomes of step (a) to an external aqueous buffer having a pH of between about pH 3.0 and about 6.0; and
   (c) heating the liposomes of step (b) at a temperature of about 30° C. to about 60° C. for about 10 minutes to 12 hours.

35. The method of claim 34 wherein the phospholipid is phosphatidylglycerol, phosphatidylinositol, or cardiolipin.

36. The method of claim 34 wherein the liposomes are multilamellar liposomes.

37. The method of claim 34 wherein the liposomes are multilamellar liposomes.

38. The method of claim 37 wherein the liposomes are FATMLVs.

39. The method of claim 37 wherein the liposome's aqueous layers have equal solute distribution.

40. The method of claim 34 comprising the additional step of extruding the liposomes of step (a).

41. The method of claim 40 wherein the liposomes are unilamellar vesicles.

42. The method of claim 34 wherein the liposomes additionally comprise a bioactive agent.

* * * * *